United States Patent
Heath et al.

(10) Patent No.: US 8,378,831 B2
(45) Date of Patent: Feb. 19, 2013

(54) SYSTEM AND METHOD FOR COORDINATED HEALTH MONITORING, EMERGENCY RESPONSE, AND MEDICAL RECORD DELIVERY

(75) Inventors: Chester Heath, Boca Raton, FL (US); Noel Guillama, Wellington, FL (US); Pedro Martinez, Boca Raton, FL (US)

(73) Assignees: The Quantum Group, Inc., Wellington, FL (US); Noel J. Guillama, Wellington, FL (US)

( * ) Notice: Subject to any disclaimer, the term of this patent is extended or adjusted under 35 U.S.C. 154(b) by 643 days.

(21) Appl. No.: 12/535,498

(22) Filed: Aug. 4, 2009

(65) Prior Publication Data

US 2010/0033332 A1  Feb. 11, 2010

Related U.S. Application Data

(60) Provisional application No. 61/086,612, filed on Aug. 6, 2009.

(51) Int. Cl.
G08B 23/00 (2006.01)
(52) U.S. Cl. .................. 340/573.1; 128/904; 600/300
(58) Field of Classification Search ......... 340/573.1, 340/539.12; 128/904; 600/300
See application file for complete search history.

(56) References Cited

U.S. PATENT DOCUMENTS

| | | | | |
|---|---|---|---|---|
| 5,441,047 A * | 8/1995 | David et al. | ................... | 128/904 |
| 5,842,978 A * | 12/1998 | Levy | ............................. | 600/300 |
| 5,963,136 A * | 10/1999 | O'Brien | ...................... | 340/573.1 |
| 6,221,010 B1 * | 4/2001 | Lucas | ........................... | 600/300 |
| 6,562,001 B2 * | 5/2003 | Lebel et al. | ...................... | 604/65 |

* cited by examiner

Primary Examiner — John A Tweel, Jr.
(74) Attorney, Agent, or Firm — Novak Druce Connolly Bove + Quigg LLP

(57) ABSTRACT

A computer-based system for providing coordinated health monitoring, emergency response, and medical record delivery. The system can include computing devices configured to process emergency-related indicators and data. The system can also include monitoring devices linked to the computing devices. The monitoring devices can monitor a particular area for the emergency-related indicators and data, where the monitoring devices detect among speech, sounds, images and other detectable emergency-related indicators. The monitoring devices can also transmit the emergency-related indicators and data to the computing devices. Furthermore, the system can include a module linked to the monitoring devices and configured to execute on the computing devices. The module can analyze the transmitted emergency-related indicators and data to determine whether there is an emergency, communicate with a monitoring service to validate that an emergency exists, and provide access to patient records to authorized personnel, based upon whether an emergency exists.

21 Claims, 3 Drawing Sheets

SYSTEM AND METHOD FOR COORDINATED HEALTH MONITORING, EMERGENCY RESPONSE, AND MEDICAL RECORD DELIVERY

CROSS-REFERENCE TO RELATED APPLICATIONS

This application claims the benefit of U.S. Provisional Patent Application No. 61/086,612, which was filed Aug. 6, 2008, and which is incorporated herein in its entirety.

FIELD OF THE INVENTION

The present invention is related to the field of health care, and more particularly, to computer-based systems and methods for providing coordinated health monitoring, emergency response, and medical records delivery.

BACKGROUND OF THE INVENTION

Significant advances in medical technologies, improved medical procedures, and ever more highly-skilled emergency response teams have provided great benefits, allowing individuals to live longer and more enjoyable lives, while also mitigating the number and severity of medical complications experienced by individuals. Despite these considerable advances, difficulties inherent in detecting and assisting at the earliest opportunity an individual experiencing a medical emergency remains a major obstacle to providing optimal healthcare.

An individual undergoing a medical emergency is often times too incapacitated to call emergency services, take a desperately-needed medication, or even alert anyone who happens to be nearby that the emergency is occurring. Too often, by the time someone who can capably assist the individual is made aware of the situation and is able to respond, the emergency has progressed to a critical stage resulting in permanent impairment or even death of the individual.

An important complicating factor is that an emergency team seeking to assist the individual is often times forced to treat the individual without any knowledge of the individual's medical history and without any access to relevant medical records. As a result, such individuals all too often suffer irreversible complications, irreparable harm, and even death. Even under the best of circumstances, whenever a healthcare provider must treat an individual without adequate knowledge of the individual's medical history and access to the individual's medical records, the result can be unnecessary, inadequate, or even injurious treatment of the individual.

As a result, there is a need for more effective and efficient mechanisms for providing emergency detection and emergency response to individuals experiencing medical emergencies. More generally, there is a need for more effective and efficient mechanisms for providing healthcare providers with access to critical medical histories and records so as to improve diagnosis and treatment of a wide array of medical conditions. Furthermore, there is a need for mechanisms to more effectively and efficiently coordinate health monitoring, to speed up emergency response times, and ensure the rapid delivery of medical records and other critical information to healthcare providers.

SUMMARY OF THE INVENTION

The present invention is directed to systems and methods for providing coordinated health monitoring and emergency detection. The invention is also directed to systems and methods that can speed up emergency response times as well as increasing the speed and security with which medical records and other critical information are delivered to healthcare providers.

One embodiment of the invention is a computer-based system for providing coordinated health monitoring, emergency response, and medical record delivery. The system can include one or more computing devices configured to process emergency-related indicators and data. The system can also include one or more monitoring devices communicatively linked to the one or more computing devices. The one or more monitoring devices can be configured to monitor a particular area for the emergency-related indicators and data, wherein the one or more monitoring devices detect one or more among speech, sounds, images, and other detectable emergency-related indicators. The one or more monitoring devices can also be configured to transmit the emergency-related indicators and data to the one or more computing devices. Furthermore, the system can include a module communicatively linked to the one or more monitoring devices and configured to execute on the one or more computing devices. The module can be configured to analyze the transmitted emergency-related indicators and data to determine whether there is an emergency, communicate with a monitoring service to validate that an emergency exists, and provide access to patient records to authorized personnel, based upon whether an emergency exists.

Another embodiment of the invention is a computer-based method for providing coordinated health monitoring, emergency response, and medical record delivery. The method can include monitoring a particular area for emergency-related indicators and data by utilizing one or more monitoring devices, wherein the one or more monitoring devices detect one or more of speech, sounds, images, and other detectable emergency-related indicators. The method can also include transmitting the emergency-related indicators and data to one or more computing devices, wherein the one or more computing devices are communicatively linked to the one or more monitoring devices. Additionally, the method can include analyzing the transmitted emergency-related indicators and data to determine whether there is an emergency, wherein the analysis can be performed by the one or more computing devices. The method can further include communicating with a monitoring service to validate that an emergency exists. Moreover, the method can also include providing access to patient records to authorized personnel, based upon whether an emergency exists.

Yet another embodiment of the invention is a computer-readable medium which contains computer-readable code that when loaded on a computer causes the computer to monitor a particular area for emergency-related indicators and data by utilizing one or more monitoring devices, wherein the one or more monitoring devices detect one or more of speech, sounds, images, and other detectable emergency-related indicators; to transmit the emergency-related indicators and data to one or more computing devices, wherein the one or more computing devices are communicatively linked to the one or more monitoring devices; to analyze the transmitted emergency-related indicators and data to determine whether there is an emergency, wherein the analysis is performed by the one or more computing devices; to communicate with a monitoring service to validate that an emergency exists; and to provide access to patient records to authorized personnel, based upon whether an emergency exists.

BRIEF DESCRIPTION OF THE DRAWINGS

There are shown in the drawings, embodiments which are presently preferred. It is expressly noted, however, that the invention is not limited to the precise arrangements and instrumentalities shown.

DETAILED DESCRIPTION

Figure 1:
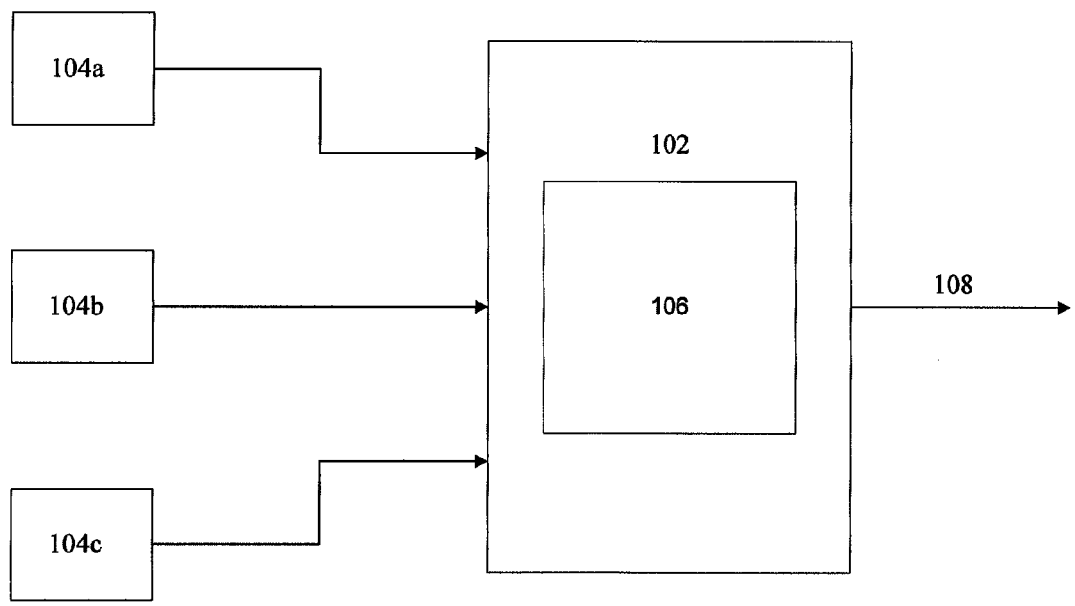
FIG. 1 is a schematic view of a system for providing coordinated health monitoring, emergency response, and medical record delivery, according to one embodiment of the invention.

Referring initially to FIG. 1, a system 100 for providing coordinated health monitoring, emergency response, and medical record delivery, according to one embodiment of the invention, is schematically illustrated. The system can include one or more computing devices 102 configured to process emergency-related indicators and data. For example, the one or more computing devices 102 can include, but is not limited to, a desktop computer, laptop, personal digital assistants (PDA), or similar type computing device or communication device having data processing capabilities (e.g., a controller, registers, logic gates, and other logic-based processing circuitry). The system 100 further can include one or more monitoring devices 104a-c communicatively linked to the one or more computing devices 102. Although illustratively, only one computing device 102 and three monitoring devices 104a-c are shown, it will be readily apparent to one of ordinary skill based on the description that a greater number of computing devices and a greater or lesser number of databases can be utilized.

The system 100 can also include a module 106 that is communicatively linked to the one or more monitoring devices 104a-c and configured to execute on the one or more computing devices 102. Alternatively, the module 106 can be implemented in hardwired, dedicated circuitry for performing the operative functions described herein. In another embodiment, the module 106 can be implemented in a combination of logic-based data processing circuitry and computer-readable code configured to execute on a particular computing machine.

Operatively, the system 100 is configured to respond whenever a person exhibits the symptoms of, or is undergoing, an emergency. The one or more monitoring devices 104a-c can monitor predetermined conditions within a particular area for emergency-related indicators and data. The one or more monitoring devices 104a-c can detect one or more among speech, sounds, images, and other detectable emergency-related indicators. For example, if a person is experiencing significant pain, one or more of the monitoring devices 104a-c can be configured to sense and record sounds and/or images that are indicative or suggestive of an emergency condition. In a particular embodiment, the one or more monitoring devices 104a-c can digitize and encrypt data captured and/or generated in response to the detection of a possible emergency condition.

After sensing emergency-related indicators and after capturing and/or generating data in response thereto, the one or more monitoring devices 104a-c can transmit the emergency-related indicators and data to the one or more computing devices 102. Once the module 106 receives the emergency-related indicators and data, the module 106 can analyze the transmitted emergency-related indicators and data to determine whether there is an emergency. For enhanced validation, the module 106 can communicate with a monitoring service (not explicitly shown) to verify that an emergency exists. If an actual emergency exists or is determined to be likely occurring, the module 106 can provide emergency responders or other authorized personnel access to patient records. For example, an Internet link can be provided to emergency medical personnel or emergency room services to connect to the monitored individual's records. The monitored individual would agree in advance to the release of records in the event of an emergency.

According to a particular embodiment, the one or more monitoring devices 104a-c can comprise one or more among a microphone, a speaker, a smoke detector, a heat detector, a device enabling encryption of the emergency-related indicators and data, a camera, a video camera, an intercom, a baby monitor, and a motion sensor. Additionally, the one or more monitoring devices 104a-c and the one or more computing devices 102 can be adapted to be portable so as to be carried by an individual and to be communicatively linked to one or more of monitoring services, offices, WiFi enabled facilities, telephone services, and mobile services. In a particular embodiment, the system 100 can be configured to implement one or more measures to ensure that the communications link and data exchanged over the link are protected against illicit and/or unwanted intrusion and access.

In another embodiment, the system 100 can include health-monitoring sensors, wherein the health-monitoring sensors can detect one or more among blood pressure, temperature, heart-rate, and other health-related patient metrics. For example, if a person is experiencing a fever, a sensor could determine that the person's body temperature is too high and relay the reading to the one or more computing devices 102. According to another embodiment, the module 106 can communicatively link to emergency services and signal an alarm to indicate that an emergency is occurring. For example, if a person has a severe wound, the system could sound an alarm so as to alert those nearby and/or send a signal to emergency services to assist the person.

In one embodiment, the module 106 can store and forward a record of the emergency-related indicators and data to one or more of the monitoring service and an emergency service. As an illustration, as the one or more monitoring devices 104a-c sense emergency-related data, the data can be stored to serve as a patient history and forwarded to appropriate emergency personnel. According to still another embodiment, the system 100 can integrate drug dispensing devices, wherein the drug dispensing devices administer drugs so as to enable remote medical maintenance. If a person is undergoing an emergency, which can be treated through the use of drugs, the drug dispensing devices can be remotely controlled so as to enable prompt treatment of the person.

Figure 2:
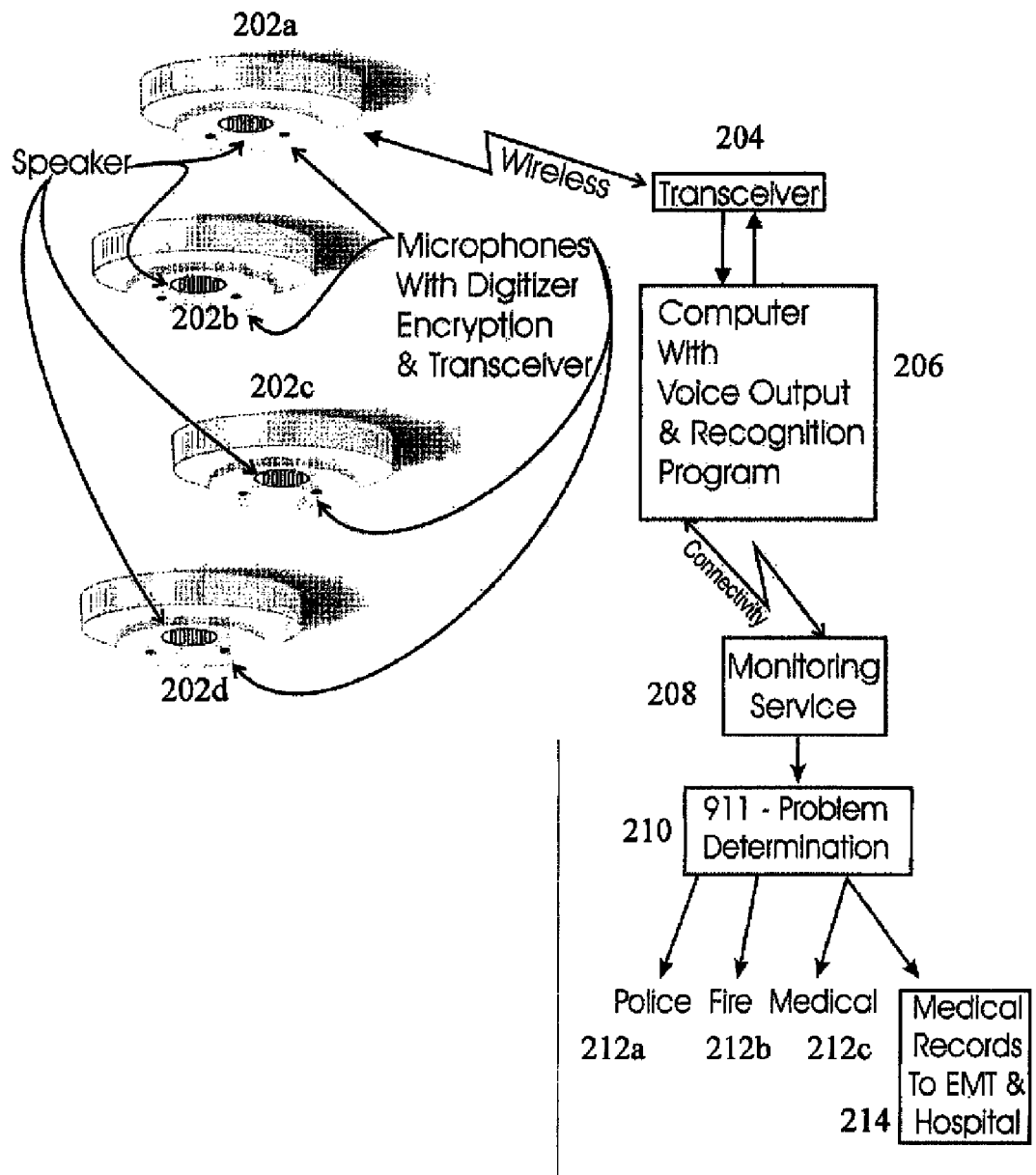
FIG. 2 is an example embodiment of a system for providing coordinated health monitoring, emergency response, and medical record delivery.

Referring now to FIG. 2, an example embodiment of a system 200 for providing coordinated health monitoring, emergency response, and medical record delivery, is shown. The system 200 can include one or more monitoring devices 202a-d and can also include a transceiver 204. The system 200 can further include one or more computing devices 206.

Operatively, when a patient is exhibiting the signs of an emergency, the one or more monitoring devices 202a-c can sense emergency-related indicators and data and can digitize and encrypt the data. The emergency-related indicators and data can then be transmitted wirelessly to a transceiver 204, which, in turn, send transmits the data to one or more computing devices 206, which contain an voice output and recognition program. The one or more computing devices analyze and interpret the data and send the data to a monitoring service 208 for validation. If an emergency is determined to exist, the monitoring service can alert emergency services 210, which can include police services 212*a*, fire services 212*b*, and medical services 212*c*. In the event of an emergency or otherwise, emergency personnel can be provided with a link to the records 214 of the person undergoing the emergency so as to enable more accurate treatment.

Figure 3:
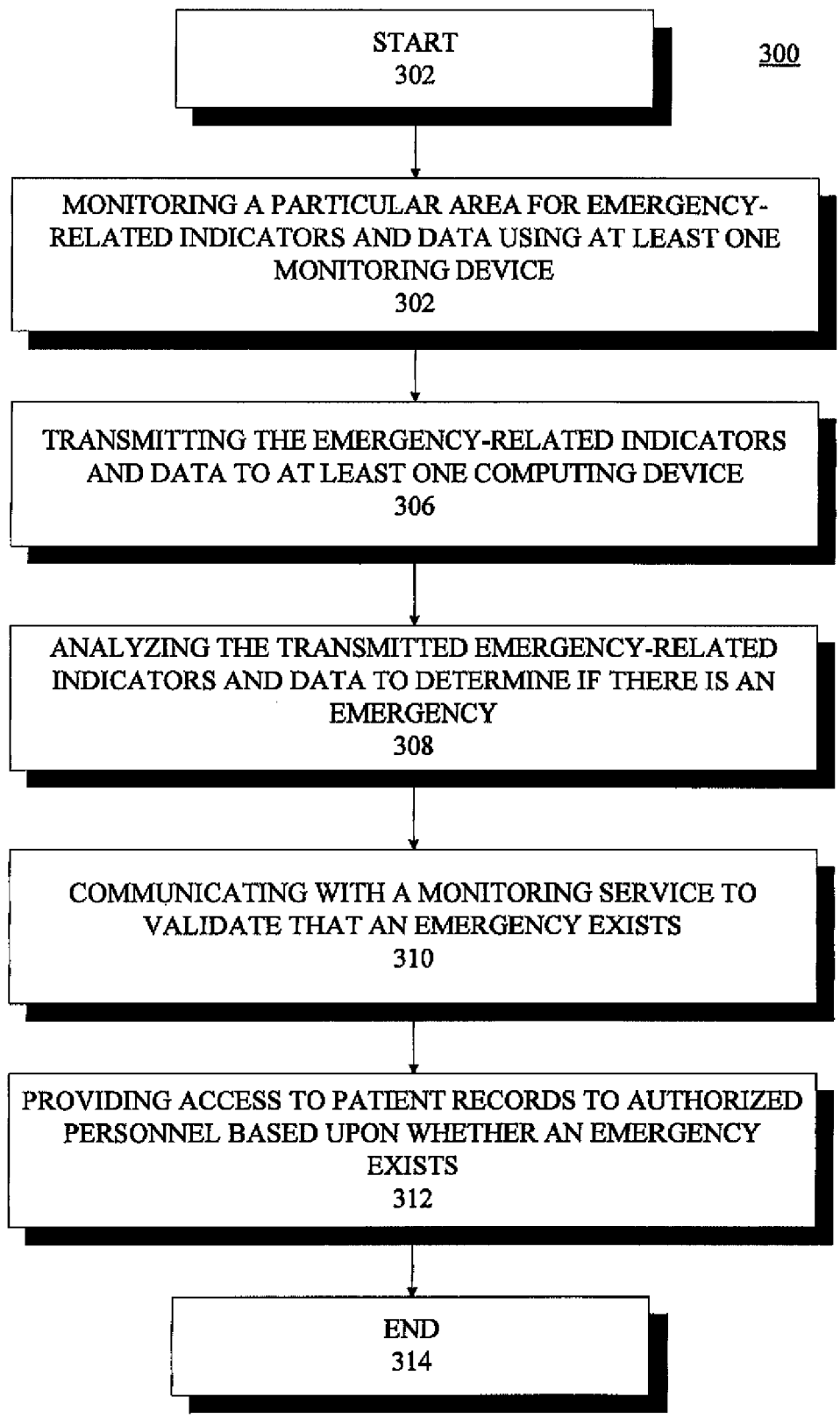
FIG. 3 is a flowchart of steps in a method for providing coordinated health monitoring, emergency response, and medical record delivery, according to another embodiment of the invention.

Referring now to FIG. 3, a flowchart is provided that illustrates certain method aspects of the invention. The flowchart depicts steps of a method 300 for providing coordinated health monitoring, emergency response, and medical record delivery. The method 300 illustratively includes, after the start at step 302, monitoring a particular area for emergency-related indicators and data by utilizing one or more monitoring devices at step 304. The one or more monitoring devices detect one or more among speech, sounds, images, and other detectable emergency-related indicators. The method 300 also includes transmitting the emergency-related indicators and data to one or more computing devices, wherein the one or more computing devices are communicatively linked to the one or more monitoring devices at step 306. Additionally, the method 300 includes at step 308 analyzing the transmitted emergency-related indicators and data to determine whether there is an emergency, the analysis being performed by the one or more computing devices. The method 300 also includes communicating with a monitoring service to validate that an emergency exists at step 310. The method 300 further includes at step 312 providing access to patient records to authorized personnel, based upon whether an emergency exists. The method 300 illustratively concludes at step 314.

The method 300 can also include, at the monitoring step 304, utilizing health-monitoring sensors, wherein the health-monitoring sensors can detect one or more among blood pressure, temperature, heart-rate, and other health-related patient metrics. For example, if a person is undergoing an emergency which does not cause the person to make a sound or move around, the health-monitoring sensors could enable detection of other signs of an impending emergency, such as elevated blood pressure, rapid heart rate, and high body temperature.

According to another embodiment, the method 300 can further include communicatively linking to emergency services and signaling an alarm to indicate that an emergency is occurring. By enabling a link to emergency services and signaling an alarm, emergency personnel and/or others in the vicinity of the person undergoing the emergency can quickly respond to the emergency and administer treatment. In one embodiment, the method 300 can include storing and forwarding a record of the emergency-related indicators and data to at least one of the monitoring service and an emergency service. For example, when the monitoring device senses emergency-related indicators and data, such as speech, images, or sounds, the data can be stored for future use and analysis and forwarded to emergency services and/or physicians for use.

According to yet another embodiment, the method 300 can include integrating drug dispensing devices, wherein the drug dispensing devices administer drugs so as to enable remote medical maintenance and assistance. As a result, those undergoing emergencies can receive prompter and more effective treatment so as to minimize the effects of an emergency.

The invention can be realized in hardware, software, or a combination of hardware and software. The invention can be realized in a centralized fashion in one computer system, or in a distributed fashion where different elements are spread across several interconnected computer systems. Any type of computer system or other apparatus adapted for carrying out the methods described herein is suitable. A typical combination of hardware and software can be a general purpose computer system with a computer program that, when being loaded and executed, controls the computer system such that it carries out the methods described herein.

The invention, as already mentioned, can be embedded in a computer program product, such as magnetic tape, an optically readable disk, or other computer-readable medium for storing electronic data. The computer program product can comprise computer-readable code, (defining a computer program) which when loaded in a computer or computer system causes the computer or computer system to carry out the different methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The preceding description of preferred embodiments of the invention have been presented for the purposes of illustration. The description provided is not intended to limit the invention to the particular forms disclosed or described. Modifications and variations will be readily apparent from the preceding description. As a result, it is intended that the scope of the invention not be limited by the detailed description provided herein.

We claim:

1. A computer-based method for providing coordinated health monitoring, emergency response, and medical record delivery, the method comprising the steps of:

actively monitoring a particular area associated with a patient for emergency-related indicators and data by utilizing at least one monitoring device to detect the emergency-related indicators and data, the emergency related indicators and data comprising at least one of speech, sound, or images associated with the particular area;

transmitting the emergency-related indicators and data to at least one computing device, wherein the at least one computing device is communicatively linked to the at least one monitoring device;

analyzing the emergency-related indicators and data to determine whether there is a medical emergency regarding the patient, wherein the analysis is performed by the at least one computing device;

communicating with a monitoring service to validate the emergency; and providing access to patient records for the patient to authorized personnel if the medical emergency is validated.

2. The method of claim 1, wherein the at least one monitoring device comprises at least one among a microphone, a speaker, a smoke detector, a heat detector, a device enabling encryption of the emergency-related indicators and data, a camera, a video camera, an intercom, a baby monitor, and a motion sensor.

3. The method of claim 1, wherein the at least one monitoring device and at least one computing device are adapted to be portable so as to be carried by an individual and communicatively and securely link to at least one of monitoring services, offices, WiFi enabled facilities, and mobile services.

4. The method of claim 1, wherein the monitoring step further comprises generating additional indicators and data for the emergency-related indicators and data by utilizing at least one health-monitoring sensor associated with the patient to detect the additional indicators and data, the additional indicators and data comprising at least one among blood pressure, temperature, heart-rate, and other health-related patient metrics.

5. The method of claim 1, further comprising communicatively linking to emergency services and signaling an alarm to indicate that an emergency is occurring.

6. The method of claim 1, further comprising storing and forwarding a record of the emergency-related indicators and data to at least one of the monitoring service and an emergency service.

7. The method of claim 1, further comprising integrating drug dispensing devices, wherein the drug dispensing devices administer drugs so as to enable remote medical maintenance.

8. A computer-based system for providing coordinated health monitoring, emergency response, and medical record delivery, the system comprising:
at least one computing device configured to process emergency-related indicators and data;
at least one monitoring device communicatively linked to the at least one computing device, wherein the at least one monitoring device is configured to:
actively monitor a particular area associated with a patient for the emergency-related indicators and data, wherein the emergency-related indicators comprise at least one among speech, sounds, or images associated with the particular area; and
transmit the emergency-related indicators and data to the at least one computing device; and
a module communicatively linked to the at least one monitoring device and configured to execute on the at least one computing device, wherein the module is configured to:
analyze the transmitted emergency-related indicators and data to determine whether there is a medical emergency regarding the patient;
communicate with a monitoring service to validate the emergency; and
provide access to patient records for the patient to authorized personnel if the medical emergency is validated.

9. The system of claim 8, wherein the at least one monitoring device comprises at least one among a microphone, a speaker, a smoke detector, a heat detector, a device enabling encryption of the emergency-related indicators and data, a camera, a video camera, an intercom, a baby monitor, and a motion sensor.

10. The system of claim 8, wherein the at least one monitoring device and at least one computing device are adapted to be readily installed or portable so as to be carried by an individual and communicatively and securely link to at least one of monitoring services, offices, WiFi enabled facilities, and mobile services.

11. The system of claim 8, further comprising at least one health-monitoring sensor associated with the patient and that generates additional indicators and data for the emergency-related indicators and data, wherein the additional indicators and data comprise at least one among blood pressure, temperature, heart-rate, and other health-related patient metrics.

12. The system of claim 8, wherein the module communicatively links to emergency services and signals an alarm to indicate that an emergency is occurring.

13. The system of claim 12, further comprising at least one monitoring device having least one among a microphone, a speaker, a smoke detector, a heat detector, a device-enabling encryption of the emergency-related indicators and data, a camera, a video camera, an intercom, a baby monitor, and a motion sensor that are WiFi connected to external systems.

14. The system of claim 8, wherein the module stores and forwards a record of the monitored emergency-related indicators and data to at least one of the monitoring service and an emergency service.

15. The system of claim 8, further comprising integrating drug dispensing devices, wherein the drug dispensing devices administer drugs so as to enable remote medical maintenance.

16. A computer-readable storage medium having stored therein computer-readable instructions, which, when loaded in and executed by a computer causes the computer to perform the steps of:
actively monitoring a particular area associated with a patient for emergency-related indicators and data by utilizing at least one monitoring device to detect the emergency-related indicators and data, the emergency related indicators and data comprising at least one of speech, sound, or images associated with the particular area;
transmitting the emergency-related indicators and data to at least one computing device, wherein the at least one computing device is communicatively linked to the at least one monitoring device;
analyzing the emergency-related indicators and data to determine whether there is a medical emergency regarding the patient, wherein the analysis is performed by the at least one computing device;
communicating with a monitoring service to validate the emergency; and
providing access to patient records for the patient to authorized personnel if the medical emergency is validated.

17. The computer-readable storage medium of claim 16, wherein the at least one monitoring device comprises at least one among a microphone, a speaker, a smoke detector, a heat detector, a device enabling encryption of the emergency-related indicators and data, a camera, a video camera, an intercom, a baby monitor, and a motion sensor.

18. The computer-readable storage medium of claim 16, wherein the monitoring step further comprises generating additional indicators and data for the emergency-related indicators and data by utilizing at least one health-monitoring sensor associated with the patient to detect the additional indicators and data, the additional indicators and data comprising at least one among blood pressure, temperature, heart-rate, and other health-related patient metrics.

19. The computer-readable storage medium of claim 16, further comprising code for causing the computer to communicatively link to emergency services and signal an alarm to indicate that an emergency is occurring.

20. The computer-readable storage medium of claim 16, further comprising code for causing the computer to store and forward a record of the monitored emergency-related indicators and data to at least one of the monitoring service and an emergency service.

21. The computer-readable storage medium of claim 16, further comprising
integrating drug dispensing devices, wherein the drug dispensing devices administer drugs so as to enable remote medical maintenance.

* * * * *

UNITED STATES PATENT AND TRADEMARK OFFICE
CERTIFICATE OF CORRECTION

| | | |
|---|---|---|
| PATENT NO. | : 8,378,831 B2 | Page 1 of 1 |
| APPLICATION NO. | : 12/535498 | |
| DATED | : February 19, 2013 | |
| INVENTOR(S) | : Chester Heath, Noel Guillama and Pedro Martinez | |

It is certified that error appears in the above-identified patent and that said Letters Patent is hereby corrected as shown below:

Title Page

Item (60) should read as follows:

-- (60) Provisional application No. 61/086,612, filed on Aug. 6, 2008. --

Signed and Sealed this
Twenty-fifth Day of June, 2013

Teresa Stanek Rea
*Acting Director of the United States Patent and Trademark Office*